United States Patent
Golay

(10) Patent No.: US 10,572,625 B2
(45) Date of Patent: Feb. 25, 2020

(54) COMBINATION DENTAL IMAGING SYSTEM AND DENTAL PRACTICE MANAGEMENT AND CHARTING SYSTEM WITH A BI-DIRECTIONAL COMMUNICATION INTERFACE

(71) Applicant: Douglas A. Golay, Coon Rapids, IA (US)

(72) Inventor: Douglas A. Golay, Coon Rapids, IA (US)

(73) Assignee: RealCloud Imaging Inc., Ames, IA (US)

( * ) Notice: Subject to any disclaimer, the term of this patent is extended or adjusted under 35 U.S.C. 154(b) by 270 days.

(21) Appl. No.: 15/486,463

(22) Filed: Apr. 13, 2017

(65) Prior Publication Data

US 2018/0039733 A1 Feb. 8, 2018

Related U.S. Application Data

(63) Continuation-in-part of application No. 14/248,348, filed on Apr. 9, 2014, now abandoned.

(51) Int. Cl.
| | |
|---|---|
| G06F 19/00 | (2018.01) |
| A61B 6/00 | (2006.01) |
| A61B 6/14 | (2006.01) |
| G16H 40/20 | (2018.01) |
| G16H 30/20 | (2018.01) |
| A61C 7/00 | (2006.01) |
| A61B 6/03 | (2006.01) |
| A61B 1/24 | (2006.01) |

(52) U.S. Cl.
CPC .............. *G06F 19/321* (2013.01); *A61B 6/14* (2013.01); *A61B 6/463* (2013.01); *G06F 19/328* (2013.01); *G16H 30/20* (2018.01); *G16H 40/20* (2018.01); *A61B 1/24* (2013.01); *A61B 6/032* (2013.01); *A61B 6/145* (2013.01); *A61B 6/563* (2013.01); *A61C 7/002* (2013.01)

(58) Field of Classification Search
None
See application file for complete search history.

(56) References Cited

U.S. PATENT DOCUMENTS

| | | | | |
|---|---|---|---|---|
| 8,416,984 B2 * | 4/2013 | Liang | ..................... | A61C 19/00 382/100 |
| 2008/0033754 A1 * | 2/2008 | Smith | ................... | G06F 19/324 705/2 |
| 2014/0067423 A1 * | 3/2014 | Joao | ...................... | G16H 10/60 705/3 |

\* cited by examiner

*Primary Examiner* — Michael Tomaszewski
(74) *Attorney, Agent, or Firm* — W. Edward Johansen

(57) ABSTRACT

A combination dental imaging system and dental practice management and charting system includes a dental imaging device, a dental practice management and charting system and a bi-directional communication interface which couples the dental imaging system to the dental practice management and charting system. The combination dental imaging system and dental practice management and charting system also includes a code generator, a translator and a correlator. The code generator generates an ADA CDT code. The translator translates the ADA CDT code into at least one property required by the dental imaging system in order to acquire dental images of a specific image type, format and quantity. The correlator correlates the dental images to be acquired by the dental imaging system to the ADA CDT code so that the dental images are acquired by having at least one property set.

6 Claims, 3 Drawing Sheets

COMBINATION DENTAL IMAGING SYSTEM AND DENTAL PRACTICE MANAGEMENT AND CHARTING SYSTEM WITH A BI-DIRECTIONAL COMMUNICATION INTERFACE

BACKGROUND OF THE INVENTION

Field of the Invention

The present invention generally relates to a combination dental practice management and charting system and dental imaging system and more particularly to a bi-directional communication Interface which couples a dental practice management and charting system to a dental imaging system.

Description of the Prior Art

Dental practice management systems have been used in dentistry since the rapid adoption of the personal computer which started in the 1980's. Originally, dental practice management systems emulated and replaced the existing dental office front desk paper systems in use previously by dentists and dental staff such as for accounting of patient bills and scheduling of patients appointments. Most dental practice management system's expanded their capabilities in the 1990's and 2000's and added features for the dentists and dental staff in the back office/operatories which included an electronic version of the paper dental chart. Electronic dental charting allowed the dentists to create an electronic record of patients existing dental conditions, in addition to procedures completed or in-process by the dental office on this patient; as well as optionally treatment planning for the patient showing various treatment options available. In addition, the practice management system allowed creating an electronic version of a dental insurance claim form, which was transmitted electronically to a clearing house or directly to the insurance company for payment of performed procedures to insured patients. This electronic claim form used standardized alpha-numeric codes which were created and maintained mostly by the American Dental Association and were generally used in the United States for submission of a claim to an insurance company for procedures performed on an insured person. Some of these ADA CDT codes required submission of evidence showing the requirement for a procedure and/or results of a procedure and therefore required pretreatment and/or post treatment diagnostic or clinical image to be attached and submitted with the electronic dental claim form and/or images which could be mailed to an insurance company separately from the electronic claim Dental practice management system and dental imaging systems have remained and mostly remain separated isolated systems. There has been minimal integration of these two disparate systems and this has limited the capability of such systems when used by dentists and their staff. A user of a practice management system who wishes to take a 4 bitewing x-ray examination on an insured patient must complete the following steps of: (1) entering a 4 shot bitewing X-ray procedure using the ADA CDT code along with a status of a completed image in the electronic charting module portion of the practice management system; and (2) entering either manually or automatically the completed image of the 4 shot bitewing X-ray procedure into a ledger/billing portion of the dental practice management system. The user must also then get to a separate disparate imaging application and first select what format of images to capture (bitewing, 4 x-rays), then acquire the actual 4 bitewing x-rays, and then optionally tag these images with tooth numbers for the teeth represented. Then the user (or another user) must create and/or edit the dental electronic claim for this patient, identify and load the proper image from the disparate practice management and imaging systems, which usually entails exporting and or copy and pasting and image or via some other non-automatic means, and finally selection of the image or images that need attached to this specific dental electronic claim form. The claim form itself was generated either automatically or manually via the user as result of the user entering the ADA CDT code in the practice management charting system in the very first step above. This scenario is repeated over and over for a normal dental practice and is tedious and requires many steps, and has added complexities by requiring use of multiple systems with disparate workflows, all of which lead to this method being cumbersome and mistake prone.

U.S. Pat. No. 8,416,984 teaches a method which generates an electronic dental chart for a patient, executed at least in part by a host processor, obtains image data for each of a number of teeth of the patient and generates a template dental chart for the patient that represents the position of each imaged tooth with a symbol according to the obtained image data. The template dental chart for each imaged tooth symbol is populated to form the electronic dental chart by associating the obtained image data to the corresponding symbol in the template dental chart for the imaged tooth, analyzing the obtained image data to identify a condition of the imaged tooth, associating at least the identified condition with the symbol for the imaged tooth, and displaying the populated electronic dental chart, wherein the displayed electronic dental chart provides a visual indication of the identified condition. Dental charts aid the dental practitioner in the systematic diagnosis, tracking, and treatment of teeth and supporting structures. Conventional dental charting is a largely manual process, performed by the dental practitioner with the help of a standardized paper template that allows written annotation related to each tooth to be recorded and stored in the patient's file. With the increased use of electronic tools for image storage and display, the value of maintaining dental charts as digital data that can be displayed as needed is widely recognized. Various types of dental charting software have been developed, such as the SOFTDENT software from Kodak Dental Systems by Carestream Health.

U.S. Patent Publication No. 2014/0067423 which teaches a computer-implemented method, including receiving and storing a note, comment, or message, transmitted from a first communication device used by an individual, a patient, or a caregiver for same, in an electronic health record, transmitting the note, comment, or message, to a second communication device used by a provider, receiving information regarding an examination finding, a diagnosis, a treatment, or a treatment plan, transmitted from the second communication device or a third communication device used by the provider, processing, with a computer, the information regarding an examination finding, diagnosis, treatment, or treatment plan, generating a report containing information regarding the examination finding, diagnosis, treatment, or treatment plan, storing the report in the electronic healthcare record, generating an insurance claim or request for payment, and transmitting the insurance claim or request for payment to a fourth communication device used by an insurer or a payer.

U.S. Patent Publication No. 2008/0033754 which teaches a method and computer program for managing and operating a dental practice. The dental practice includes a computer system having an application server and a database. The method and computer program include inputting patient data via a web browser into the application server, encoding the one or more operations using a non-proprietary format, storing the patient data and the encoded one or more operations in the database and displaying to a user the patient data in the web browser. The patient data includes one or more operations.

U.S. Pat. No. 7,010,153 teaches a method which identifies teeth on a digitized X-ray picture by using image processing algorithms to localize areas containing the teeth by segmenting and/or edge detection. These areas are computationally linked with parameters of the X-ray unit and, optionally, with patient-heightened specific parameters. Another method assigns information to teeth determined in either a digitized X-ray picture or in a schematic representation and includes a first step of detecting the digitized X-ray image for the schematic representation and a second step of determining teeth manually or automatically ensues in the event these teeth have not yet been determined. The method also includes a third step of selecting the tooth for which additional information should be stored, retrieved or deleted and a fourth step of storing a reference to be followed for a query operation to determine the information displayed by using such reference.

US Patent Application No. 2009/0177495 teaches a system for personal medical care, intelligent analysis and diagnosis which includes at least one source of medical information; at least one source of personal medical data for at least one patient and one or more servers. The medical information and the personal medical data are accessible to the server(s). The server(s) may include: an artificial intelligence (Al) component for analyzing the personal medical data with the medical information and identifying at least one issue requiring follow-up by the patient or by at least one external authorized entity; and at least one real-time communication link for bi-directional communication with at least one external authorized entity. A storage medium stores the personal medical data for at least one patient and a bi-directional communication interface for communicating with the system as one of at least one external authorized entity. Physicians have long maintained a medical record for each patient. These medical records have conventionally resided at the physician's office in a records area. When a patient changes physicians, unfortunately, absent making a copy of the patient's medical records and transporting the copy to the next physician, there is no easy way to provide a new physician access to the patient's prior medical history. Electronic medical records have been developed to help heath care providers in caring for their patients. Unfortunately, since no standards exist, compatibility, exchangeability and accessibility of medical information is not conventionally possible among health care providers. Conventionally, there are many databases around the world with patients' medical records, stored and locked up in proprietary formats, in doctor's offices, hospitals, government agencies, or third party payer's warehouses that are not readily accessible to a patient, or the patient's current physician. While this medical information may be very useful in the management of the patient, there is no conventionally available method for the medical information to reach the entities that could help that patient (e.g., physician, hospital, public and provide entities, offices, and thirty party payers) in a timely fashion, as would be needed, particularly in the case of emergency patient care needs. Efforts to attempt to bring standardization of medical records in a universal medical record form and electronic medical record systems have made access to medical information easier.

However, the main problem of obtaining data when the physician, hospital, insurance company, or the patient needs it, in a timely fashion, has remained an obstacle. Most medical records are currently stored in a doctor's office, hospital, or a database that are not always accessible to the patient when the patient or patient's health care giver need the information. While most records may be in a physician's office or a hospital, and some few medical records are stored in an electronic or digital medical record system, very few doctors, patients, hospitals, or insurance providers have access to these medical records in an urgent setting, especially if the patient is traveling, away from the patient's residence and normal health care provider. Another problem with conventional electronic medical records is that conventional medical record databases are generally redundant and incomplete. Updating and maintaining the databases is labor intensive and usually the database serves certain designated purposes for which it was programmed rather than being a complete medical record for the patient. A hospital may contain several databases for a patient's medical records, one designed for accounting/billing, another relating to recording patient symptoms, and others for laboratory results, for example. Current physicians' lack of access to a patient's past medical records is a leading challenge in treating patients referred for care by a consultant. Quite often the patient's medical record is in the primary care provider's office and is thus inaccessible to the current physician handling the referral. For numerous reasons, such as office closings or inability to locate the chart in a timely manner, duplicate testing, and diagnosis may occur as a result of lack of access to critical medical information of the patient. Repetitive testing may often be performed, particularly in the case of urgent therapy, where lack of access to this information may be most critical, such as, for preoperative surgical clearance. Access to information is also hindered by the fact that even when having access to pertinent medical information, the sheer volume of information in conventional records makes cumbersome the access of critical information from medical records. A better way of obtaining summarized, merged, up to date information about a patient is not available to a patient or the patient's health care providers, using conventional systems.

Since the drafting of the Medicare Prescription Drug, Improvement, and Modernization Act of 2003, prescription error reduction has become one of the important mandates for the medical industry as well as for the government and private health care sectors to improve health care delivery. Also, laboratory results frequently require changing of the medication regimens to avoid potential toxicities, drug interactions and side effects for the patients. The dispersion of a patient's medical records can make it difficult to identify and correct such potential undesirable drug interactions.

Even in cases where all of the relevant records are co-located, a physician or pharmacist may still miss the potentially harmful interactions. Further, the distribution and inaccessibility of a patient's whole health and medical record, combined with limited time for office visits, may prevent a treating health care provider from being able to identify secondary issues that may aid in diagnosis and treatment.

What is needed is a system, method, and computer program product which may be adapted to provide a patient a portable, digital medical record, which may be carried by the patient so access to the patient's medical information will always be available. This previously unfulfilled need is particularly in demand in emergency situations, when a health care provider has only a limited time to diagnose an illness and provide care for a patient, in life threatening peril.

US Patent Application No. 2012/0162401 teaches a unified imaging platform which can be adapted for use with a variety of medical imaging devices. The unified medical imaging platform can include a display, a processor, a data storage device and one or more external interfaces. The unified imaging platform can be removably coupled to a medical imaging device such as an endoscope. The unified imaging platform can be coupled to the medical imaging device via a wired or wireless link. Using web services, the unified imaging platform can also transfer image data to other devices including a local desktop computer system, a mobile device and/or a remote system. A medical imaging system includes a router module wirelessly transmitting image data to a tablet PC or other distinct display device. The tablet PC may communicate corresponding image data to another tablet PC via a wireless telephone network. A medical imaging system includes an endoscope having a main body portion with a proximal end and a distal end, n insertion tube which is coupled to the main body portion and has a proximal end and a distal end, an image sensor unit which is disposed along the insertion tube, an electrical link electrically which couples the image sensor unit to the main body portion, a router module which is in communication with the image sensor unit, the router module and which is configured to transmit via wireless transmission image data corresponding to images captured by the image sensor unit, an external computer which includes a transceiver for receiving image data transmitted from the router module via wireless transmission, a memory for storing received image data and a display device for displaying images captured by the image sensor unit. The endoscope includes an image processor coupled to at least one of the electrical link and the router module. The router module is configured to transmit image data processed by the image processor. The router module transmits raw image data to the external computer, and wherein the external computer further includes an image processor. The external computer's display device is configured to display image data processed by the image processor. The router module is configured to transmit data to the external computer via a WiFi connection and to enable bi-directional communication with the external computer. Manufacturers have attempted to produce digital archiving platforms to allow easy integration into the digital age by integrating disc burners and hard drives into the endoscopy units so that exams can be stored directly onto removable media. These alternatives, however, limit editing of the images and are not very dynamic. Other manufacturers have attempted to produce endoscopy units that capture the images directly into a proprietary computer system designed for the specific function of video capturing and archiving. These systems provide better data manipulation, but can cost more than $20,000.00, and thus not affordable for a small or cost-limited practice.

US Patent Application 2007/0143164 teaches a business practice management system which includes a client contact management workflow made up of multiple stages of interaction between users of the system and clients of a business practice. Tasks, events, forms, and conditions of the stages provide conditions for moving from one stage to another, and define interactions between the users of the system, the clients of the business practice, and information relating to the assets of the business practice. A global business practice management workflow can also be included to manage assets as needed independently of client contact stages. User interfaces employ the workflows to interactively direct users of the system in managing multiple categories of assets of the business practice, including employees, client accounts, inventory, and records.

Today's business practices need to manage various types of assets, including inventory, employees, client accounts, and records. Automating this management is a difficult task. Previous attempts to automate business practice asset management has led to a number of expensive, inadequate, mismatched tools that quickly become obsolete. What is needed is a business practice management system that manages various types of assets of a business practice in an integrated fashion, has the flexibility to be implemented with a wide variety of business practices, is easily adaptable to changes in needs of business practices, and can be delivered to the business practice without requiring investment in equipment or products.

US Patent Application No. 2014/0046692 teaches that for those experienced with medical and dental practice management there exists a substantial need for better communication across medical/dental offices as pertains directly to mutual patient treatment and care. Here is a straightforward way to better serve the patient and improve practice efficiency through the design of a single, centralized system for which to manage all patient referrals in their practice. The management systems are easy to use, reliable and created by medical/dental personnel for medical/dental personnel to provide cost savings, increase practice production, and most importantly, improve the patient experience. A web-based patient referral management program and accompanying services is a web-based method of sharing and managing mutual patient information and tracking treatment progress of a patient by all attending doctors, dentists and laboratories in real-time.

Currently a significant communication breakdown across general and dental specialist providers (endodontists, orthodontists, etc.) exists in the form of limited shared mutual patient treatment information. At present, most dental practices use differing practice management software specific to their particular needs and as such the method of sharing such information is restricted to phone, fax, email, postal mail or patient delivery. Without a centralized process with which to access, exchange and update patient information, documentation is often lost, misinterpreted, of poor quality, and vulnerable to unauthorized alteration.

There exists a significant need for a more effective method of sharing mutual patient information and tracking treatment progress across all attending doctors, dentists, laboratories and related healthcare providers. This communication barrier across attending doctors, dentists and laboratories can best be remedied by the sharing in real-time of patient information through a web-based program (website) and corresponding application.

US Patent Application No. 2011/0153659 teaches a method of operating a centralized healthcare management system that includes a data translation map database and a central interpolation server computer interconnected to a computer network. The central server references a data translation map database for a desired translation map that enables the central interpolation server to translate data records from a source format to a destination format. The provision of medical and related management and monitoring services, uses a central server in conjunction with locally distributed legacy servers, systems, devices and databases for managing and monitoring healthcare services, payments, costs, risks, quality control, and performance measurement. The healthcare industry today is a complicated and fragmented system. People at different times require the services of various types of healthcare providers, such as doctors, home care nurses, dentists, surgeons, therapists such as physical therapists and the like. People will utilize these services as needed or on an emergency basis, or often on recommendations of others. As a result, people will tend to use such healthcare providers that have no relationship with one another, which results in fragmented healthcare management. For example, a person may have medical records on file with a general practitioner doctor, a number of specialists and their dentist. This can lead to redundancy of paperwork, increased human error, which in turn can lead to mistakes in providing care, for example when one healthcare service provider does not have a complete record of a patient's medical history and makes an incorrect diagnosis or recommendation as a result. Mistakes can also occur when a patient visits a new doctor and provides erroneous background information. Expenses are driven upwards when healthcare service providers try to obtain prior records such as x-rays in order to dispense treatment. It is estimated that 20% of diagnostics are redundant since the required information is not in the right place at the right time. These issues also lead to delay in obtaining treatment. As a result, many people will not seek appropriate medical treatment (including preventative care and maintenance) because it is too inconvenient, cumbersome, confusing, and time-consuming. It is critical to provide the required information at the point-of-care, such as in emergency room care with a patient having no medical records immediately available or in ambulatory care. The patient-specific issues mentioned above are also problematic from the viewpoint of the healthcare service provider. In addition, the healthcare service provider is usually paid by a health insurance company or other third party (such as a credit union), which adds many more problems such as inordinate delays in getting paid, increased paperwork, and even non-payments in some cases. This increases the cost of providing services and takes away the providers' time that could otherwise be spent tending to their patients. Healthcare insurers also face problems such as insurance fraud (for example where claims are made for services not rendered, excessive testing, improper prescriptions, etc.) and the increased cost of processing the insurance claims from the healthcare service providers as well as patients. Healthcare service centers such as hospitals, as well as their patients, also face similar problems. Persons desiring to obtain medical care, for example in an emergency situation, often encounter long delays in getting appropriate treatment. Delays may be attributed to several factors. One factor is the requirement for a patient to fill out forms at the emergency room intake, including personal information (e.g. name, address, telephone number), past medical history, and insurance information. This type of information is static since it generally does not change based on the emergency at hand. Other information that must be provided is situation-specific, such as the symptoms encountered by the patient at the time of the particular visit to an emergency room or other healthcare provider. Delays are further encountered when the emergency room personnel must process the information provided by the patient, such as when they must verify the validity of the insurance information given, or if no information is provided. Delays such as these can have significant consequences in situations where care must be immediately provided. Even in those non-emergency situations, long delays in obtaining appropriate care is undesirable.

US Patent Application 2007/0198596 teaches a system that processes textual messages which are integrated with at least one digital attachment. This system is useful in the electronic filing and processing of image data and of textual data associated with the image data. One particular application of this system would be for the electronic filing and processing of dental x-rays with patient claim forms. An attachment integrated claims (AIC) system prepares and processes forms with integrated attachments such as digital insurance claims including Prior Approval Claim (PAC) applications containing both a text form and an integrated digitized attachment. High administrative costs for filing and processing health insurance claims have been the bane of the health insurance industry from its inception. Over the years, many attempts have been made to develop a faster and more cost effective claims processing system. Three stages in this development effort are described in the following correspondingly numbered paragraphs:

(1) The original system involved hard copy paper claims only, with transmission and all processing done manually. Originally, an insurance claim was filed by the patient or the health care provider filling out a paper form. The completed paper form was then mailed to the insurance company. At the insurance company, the paper claim form went through a series of administrative steps, all the time remaining as a hard copy paper object. When a decision was made, the decision was written up and archived with the claim form; a hard copy was also sent to the patient and/or provider along with the payment. (2) The first significant advancement resulted from the introduction of the mainframe computer. This allowed for electronic processing within a given insurance company, i.e., once the claim was on the computer inside the company, the paper form could be dispensed with. Computerization is a highly effective way of reducing administrative overhead in claims processing.

Thus, mainframe computers were purchased and installed internally at the insurance companies. Since these computers were intended for internal use only, each company thought only of its own needs and had its claims management software customized. While the claims management software for a number of insurance companies would be written in the same high-level programming language, e.g., COBOL, the similarity between software programs often ended there. There were many virtues to these early systems, primarily with respect to decreased administrative costs, but a major drawback was that the data for each "paper" claim had to be entered into the computer to form an electronic claim. This necessitated the manual transcription of exactly the same information that had been handwritten into the original paper claim before it was sent to the insurance company.

(3) The next advancement was the electronic filing of claim forms. This was made possible by the introduction of the personal computer and modem into the provider's office. The main purpose of this stage was to eliminate the manual re-entry of information into the insurance company mainframe.

The basic idea was to have the providers fill out an electronic claim form, instead of a paper claim form. This electronic form, which would be stored in the memory of their PCs, would then be transmitted, as a computer file, to the insurance company. It could then be integrated directly into the electronic claims processing system without the manual re-entry of data. Thus, the technology existed to produce a system that computerized the overall filing and processing of the insurance claim from the point of entry, the provider's office, to the final report of the claims adjuster.

Although the idea was straightforward, implementation was not. Two basic problems had to be overcome in order to create a viable system. First, the information contained in the electronic claim form had to be integrated into the claims processing software at the insurance company. Second, a majority of providers have to be able to interface with a majority of insurance companies, i.e., insurance company mainframe computers. However, because of the way computers had entered the insurance industry originally (stage #2), there was no industry-wide standard, i.e., the legacy mainframe computers of the different insurance companies were incompatible. This was true both with respect to the type of software used and with respect to the information that each company required on its claim form.

One attempt to deal with these problems was the creation, by a consortium of insurance companies, of the National Electronic Information Corporation (NEIC). NEIC's basic function is that of a clearinghouse. It interfaces between the insurance companies and the service providers. It also establishes rigid standards that must be met in order to transmit an electronic claim form to an insurance company. In practice, the service provider sends an electronic claim to a vendor, who performs a service such as screening of the form. The vendor then transmits the form to NEIC, which then re-transmits it to the patient's insurance company. Since it is a computer file, the information in the electronic claim form can then be entered directly into the company's mainframe claims processing system, without the manual re-entry of data, and then processed.

Thus, a coherent system was created that allows for the electronic filing, transmission, and processing of insurance claims. This system is employed by thousands of providers and hundreds of insurance companies.

NEIC was designed to act as a clearinghouse for claims that are 100% text and that conform to very restrictive formats. For claims that meet these conditions it functions well, resulting in substantial savings on administrative costs for the insurance companies. It has been estimated that going to this third stage system results in savings of as much as 60% in claims processing costs.

But there are many claims that do not meet these conditions. These would include claims that require additional text information that doesn't fit into the prescribed format and/or claims that require non-text information. In general, these are called "claims with attachments." "Attachments" are any additional information that must be sent with the "standard text claim form." This could include: pictures, graphs, additional text not allowed on the standard claim form and sound recordings. An example of such a claim would be the PAC (Prior Approval Claim), which may be alternately denoted as a "Pretreatment Claim". These are claims that are sent to the insurance carrier before a procedure is performed. For example, pretreatment claims are often required by dental insurance companies on any procedure over a specified amount, e.g., $200.00. The aspect of this type of claim which renders it incompatible with the present electronic claim processing system is that the insurance companies require that additional medical evidence be included, i.e., attached to, the text part of the claim form.00 In an exemplary case, the additional medical evidence is an x-ray. The goal of the insurance company is to review the claim, i.e., both the text form and attachment, and to do so in a cost effective manner. The natural next stage in the development of claims processing systems is to attempt to computerize this process. Scanners are now available that can digitize a dental x-ray, i.e., convert it into a computer file that can be viewed on a monitor. But transforming the medical evidence into digital form is not enough to facilitate electronic processing of claims with attachments. One must also take into consideration the existing claims processing infrastructure, i.e., the legacy infrastructure. The difficulty with trying to include a digitized x-ray for processing with an electronic claim form, within the current infrastructure, is multifaceted. First, NEIC does not at the present time allow this type of information to be transmitted through NEIC to the insurance companies. Second, with the current system, the claims adjusters access claims information through terminals connected to mainframes. But there is the inherent problem of displaying images on mainframe computers. This is especially true of mainframe computers running software written in business programming languages such as COBOL. It might be thought that a solution to this problem would be to replace the terminal with a PC. Although many personal computers provide the graphics support needed to display the digitized x-ray, there are significant problems in interfacing a PC with a mainframe computer. For example, in order to interface with the mainframe computer, PCs often run terminal emulation software which permits the PC to act like a dedicated, dumb terminal attached to the mainframe computer. Terminal emulation software is notoriously lacking in graphics capability. And finally, getting a digitized x-ray from one provider to one insurance company is not all that is needed. Rather, what is really needed is an industry-wide system whereby a provider can interact with any insurance company. This results in a massive interfacing problem since there are multitudes of insurance companies using different legacy hardware systems and company unique software.

Each time a way has been found to more fully utilize computers in claims processing systems, the administrative costs associated with claims processing have gone down. However, in the area of "claims with attachments," no coherent industry-wide system exists that allows for the integrated filing, transmitting and processing of these claims electronically, i.e., via computers. Thus, when attachments are required, providers are forced to submit hard copy claim applications, while insurance companies labor under an administrative system that is a hybrid between a manual and an electronic system, i.e., a hybrid between stage #1 and stage #2. This hybrid system, which is described in greater detail below, is labor intensive, prone to problems, and slow. For providers, insurance companies, and patients, this is a time-consuming, costly and irritating process. In short, there is at least one type of insurance claim that has not, until now, been able to avail itself of the third stage of computerization, as described above. In fact, there are even difficulties with the second stage. This group includes any claim whose "standard text form" must be accompanied by additional information that does not fit into this standard format, e.g., x-rays, EKGs, additional text information such as Operating Room Reports. In general, these are referred to as "attachments." One primary example of this would be Prior Approvals for dental procedures. Prior Approval Claim (PAC) applications are those claims that are submitted for the purpose of receiving a predetermination of benefits from the insurance company for a procedure that hasn't as yet been performed.

In the area of Prior Approval Claims, the goals of the insurance companies are to validate the necessity of the procedure and to determine whether the patient's insurance policy obligates the insurance company to pay for such a procedure. This requires that the insurance company itself review the medical evidence. For an insurance company's in-house dentist, for example, to make this appraisal, the dentist is required to review both the "text form" and the accompanying x-ray of the patient. However, the presence of a film x-ray means that electronic claims methods cannot be implemented. The savings associated with electronic claim processing is not available with respect to Prior Approval Claim forms. Nationwide, there are approximately 200,000 dental PAC applications filed per week. Roughly, for every PAC application there will be eventually a Final Payment Claim (FPC) form submitted when the medical procedure is completed. It is estimated that the overall administrative cost is $25 per PAC form and $10 for the Final Payment Claim. It is also estimated that if a coherent electronic system could be implemented, it would reduce these administrative costs to $15 per PAC application and $5 per Final Payment Claim. The savings could amount to as much as $3,000,000 per week collectively for the health care industry for dental PAC applications and FPC forms alone.

By using the DIN on the x-ray, the reviewing dentist downloads, from the mainframe computer, the textual part of the patient's PAC application. The dentist makes a decision, records it in the memory of the mainframe computer, and has a hard copy of the Predetermination form posted back to the provider. Once the procedure has been completed, the provider's office completes the Predetermination form, or fills out a separate Final Payment Claim (FPC) form. This is then posted to the insurance company. During step S1, the dentist decides that a costly procedure is necessary for a patient whose insurance carrier requires prior approval for such treatment. During step S2, the dentist provides the patient with his diagnosis and gives the patient an estimate for performing the recommended procedure. The dentist then asks the patient to contact his insurance carrier, or plan administrator at work, to obtain the necessary PAC form. During step S3, the patient completes that portion of the PAC form that pertains to him, signs the form, and sends it to his provider. After the PAC form arrives at the provider's office at step S4, one of the office personnel retrieves the patient's file and the PAC form at step S5, extracts the patient's x-ray, either the original, a copy of the original, or a second, previously taken x-ray, during step S6, and the PAC form is filled out entirely by hand, i.e., the information about the provider has to be entered every time a new PAC form is received, during step S7. Copies of the completed form are made and are placed in the patient's file during step S8. The envelope containing the PAC form is addressed to the appropriate insurance company at step S9. The form and the x-rays are placed in the envelope during step S10. An entry is made in both the patient's computer file (if the provider's office is equipped with one) and his hard copy file indicating that the PAC form has been sent during step S11 and, finally, during step S12, the envelope is mailed. The envelope meanders through the U.S. Postal Service for several days at step S13 until the envelope finally arrives at the mail room of the insurance company at step S14. In the mail room, the envelope is opened at step S15, the data from the PAC form is entered into the insurance company's mainframe computer and is given a Document Identification Number (DIN) that identifies the patient and the current claim application at step S16. During step S17, the x-ray is labeled with the same DIN. It will be appreciated that the DIN on the x-ray and in the document now on the mainframe computer must be identical. It will also be appreciated that for some insurance companies, this manual processing is contracted to an outside agency, which would require several more steps, which steps will not be described further. During step S18, the x-ray is manually forwarded to the reviewing dentist's area. During step S19, the PAC form is transferred to a directory and waits to be read by a reviewing dentist. During step S20, a group of x-rays arrives from the mail room at the reviewing dentist's area. A film x-ray is pulled out of the waiting pile by the dentist during step S21 and the reviewing dentist then accesses the "PAC form" directory during step S22 by, for example, reading the DIN from the x-ray and typing the DIN into the computer. The electronic PAC form corresponding to this x-ray is located in memory and downloaded to the reviewing dentist's monitor during step S23. The procedure requested is read off the terminal monitor and the film x-ray is reviewed during step S24 and a determination is made during step S25. It will be appreciated that a determination refers to either an approval or a denial of the request. Assuming that the procedure is approved, either a statement or explanation of benefits (EOB) is also generated. For the purposes of this discussion, it will be assumed that the procedure is approved. A denial would necessitate a parallel but alternative set of processing steps, which steps will not be further described. During step S26, the insurance company's Predetermination form is filled out either electronically or by hand. For an electronic Predetermination form, the form is saved to the memory of the insurance company's mainframe computer during step S27. The x-ray is returned to the mail room during step S28. Following approval, a paper copy of the Predetermination form is made during step S29. An envelope is then addressed to the referring dentist and the Predetermination form is placed in the envelope during step S30. During step S31, the corresponding x-ray is matched with the Predetermination form and, during step S32, the corresponding x-rays are placed in the envelope. The envelope then goes back into the U.S. Postal System during step S33. Some days later, the envelope finally arrives at the dentist's office and is opened during step S34. The results are noted in both the patient's paper file and computer file during step S35, the x-rays are returned to the patient's paper file at step S36, and the patient is notified of the approval and a date is set for performing the approved treatment during step S37. The treatment is completed during step S38 and the Final Payment Claim (FPC) form is filled out during step S39. It will be appreciated that the Final Payment Claim form, for many insurance companies, is merely a subsection of the Predetermination form generated in step S29; alternatively, the Final Payment Claim form could be yet another form supplied by the insurance company. The Final Payment Claim form is then sent back to the insurance company with a copy of the signed Predetermination form during step S40. The Final Payment Claim form enters the mail room as a paper form and the final processing begins during step S41. It will be appreciated that the processing of the Final Claim Form typically requires making several entries in the information stored on the mainframe computer 350 and may require the preparation of one or more forms needed to authorize payment of the final claim. However, since an attachment is not normally associated with the Final Claim Form, additional discussion regarding disposition of the Final Claim Form within the insurance company will not be provided. Thus, the hybrid system under discussion is one that starts in the provider's office when a patient is told that a PAC form is needed and continues until the procedure has been completed and a Final Payment Claim form has been submitted to the insurance company for payment. It will be appreciated that a myriad of problems and inefficiencies arise due to claim processing in accordance with the hybrid system. The principal problems are as follows: In summary, the current method for handling PAC applications is a hybrid system somewhere between a Stage 1, a totally paper-based manual processing system, and a Stage 2 internally computerized insurance company processing system. It is part electronic and part hard copy. Also, each form must be handled twice, once as a hard copy and once as an electronic copy. This is the source of a great many of the above described problems. Moreover, the current hybrid method is costly. The process starting at the provider's office, continuing through the insurance company and finally to the return of the Predetermination form to the provider has been estimated to cost $25.00. Furthermore, the whole process is filled with potential for error, frustration, wasted time and money. The workflow for the filing and processing of a PAC form was described above with respect to the dental health insurance which was used, by way of example, to illustrate the circuitous process involved when a hard copy attachment is present. Other types of claims, or attachments, or different insurance companies might require slightly different steps. For example, instead of returning an attachment, as described above, the attachment might need to be microfilmed and archived, or some of the information contained in the attachment itself might need to be entered into the mainframe. Regardless of these differences, there are similarities in the problems that arise in processing such claims. There is a desire to overcome the problems associated with the above-described hybrid system for processing "forms with attachments." The intent was to create a coherent system that allows for the electronic filing, transmission, and processing of these forms, e.g., claims. That is, a system that would create a Stage #3 level of computerization for "forms with attachments." More specifically, the present invention was motivated by the desire to eliminate, to the maximum extent possible, all processing steps described above which are in any way connected with the presence of a hard copy attachment. The system allows for the electronic filing, transmission, and processing of "insurance claims with attachments" thereby overcoming the many deficiencies of the hybrid system claims processing methodology described above. A PAC form processing system minimizes the necessity of manual data entry. Only about 40% of the information needed to complete the PAC form has to be entered by hand. The amount of information that has to be manually re-entered by an operator is essentially zero.

US Patent Application 2007/0265887 teaches an electronic business process which includes a remittance component for automatically converting paper and electronic remittance and payment data into validated electronic information that is compliant with HIPAA Administrative Simplification standards; an electronic health record component for updating personal and electronic health records of a patient receiving treatment from a health professional. A dashboard component provides reporting functions to at least one patient, the health professional and a payer of fees for the treatment. The remittance component creates a balanced remittance that includes reason and remarks codes as pulled from the payer's explanation of benefits. A comparison of claim to remittance to payment is conducted prior to passing on to the provider's practice management system. The enhanced information is gathered in a centralized database to allow the system to create a remittance that will auto-post into the practice management system at a higher percentage than if only processing the payer's electronic remittance advice without the enhanced information. In an effort to achieve efficiencies in the delivery of healthcare in the anticipated increase in use of Medicare resources beginning in 2011, the federal government is spurring increasing adoption of new technologies, such as "certified" electronic health records (EHRs), The federal government also is encouraging adoption of electronic business processes as part of its Administration Simplification regulatory requirements that are part of the Health Insurance Portability and Accountability Act of 1996 (HIPAA). These technology and regulatory initiatives affect all healthcare stakeholders, including covered entities such as health plans, healthcare clearinghouses, and healthcare providers; their business associates; patients; vendors of electronic healthcare service systems; and banks, which will process over $2 trillion of projected healthcare expenditures in the United States in 2006. The push to adopt new technologies into the healthcare market has significantly increased the demand for remittance solutions by healthcare practitioners and increased the role of banks, especially large national banks, in the healthcare market. A continuation and acceleration of these activities is anticipated in support of new consumer-directed health plans, such as health savings accounts (HSAs) and in banks solidifying their healthcare customer bases by offering or facilitating the offering of electronic business solutions that minimize cost (health plans) and enhance cash flow (healthcare providers). In addition to adoption of remittance solutions, the healthcare market is beginning to accelerate the deployment of electronic business applications that will be encapsulated in electronic health record and practice management systems for healthcare practitioners in both dental and medical arenas. Up until now, many electronic medical record (EMR) systems were nothing more than electronic filing cabinets in practitioners' offices. These systems must be distinguished from electronic health record (EHR) systems which can communicate data content between practitioners and between practitioners and patients, in an interoperable system. Over the past several years, the demand for remittance solutions by healthcare practitioners and the increasing role of banks in the healthcare market have continued to increase. The anticipated continuation and acceleration of these activities in support of new consumer-directed health plans, such as health savings accounts (HSAs) and in banks solidifying their healthcare customer bases by offering or facilitating the offering of electronic business solutions that minimize cost (health plans) and enhance cash flow (healthcare providers) thus creates a need for new standard EHR applications, along with a need for integrated solutions in the form of electronic business applications configured for markets including the healthcare market.

Many diagnostic methods refer to individual details such as individual teeth, of which the existence, shape, and position differ individually. Diagnostics and documentation are hampered by the fact that the users are forced, when performing further actions, to resort not to individual but to general diagrams such as the standard tooth scheme on the health insurance certificate. When making automated series of radiograms is it necessary to previously inform the operating program as to which teeth are to be inspected. The solution to this problem is at present either inadequate or complicated since it is only possibly to select either entire conventional fixed groups of teeth or only individual teeth. In all cases the contact with reality is lost, since the user must leave his usual environment, e.g., a real dentition radiogram. Panoramic radiograms serve the purpose of quickly providing an overview of the general condition of the dentition. Such images can provide information without the need for other, e.g., intraoral, X-ray images. However, these findings refer not to the entire image but to a specific displayed object, e.g., a certain tooth. This thus gives rise to several findings referring to one image and to which, for example, the individual teeth are assigned. Acquisition thereof is complicated, because as a rule the user no longer has direct contact with his accustomed environment of a panoramic image. There is a need for automatic tooth charting methods and apparatus that can generate an appropriate dental chart for a particular patient from dental images and populate the generated chart with information obtained from applying automated diagnostics to the tooth image data. Dental imaging systems have been used in dentistry to generate images of teeth, jaw and facial features in both color and grayscale, in 2D and 3D, and for both intraoral and extraoral types of images for many years. These images are used for several purposes including diagnostic, treatment planning, simulations, and patient education.

US Patent Application No. 2006/0285636 teaches a computer system which generates panoramic dental images and related dental charts. The computer system allows a user to specify which images the computer system should use for generating the panoramic image. The computer system then generates a panoramic image. An image-based chart and a graphic-based chart can be generated from the panoramic image. A user can input chart data on the charts using one or more input devices. A user can also select an option to have the computer system import chart data from an external source and display the data on the charts. Any inputted and imported data are displayed on the applicable chart for the user to view and analyze. A user can toggle between the individual images, the panoramic image, and the charts. A user can overlay one image or chart over the other. A user can also replace an individual image in the panoramic image. Dentists often do not have electronic access to the charting information they need in the operatory or lab environment itself. While dentists typically have access to a computer, the computer is typically located in an office outside of the operatory or lab and does not include software that is designed to work in an operatory or laboratory. These dentists may also have access to various paper-based sources within the operatory or laboratory such as paper-based charts. However, these various paper-based sources are difficult to analyze together in a meaningful fashion. The paper-based sources have to be later inputted into the computer system outside the operatory or laboratory for electronic analysis. There is a need for improved systems and methods for image charting so that dentists can have better access to resources that assist in analyzing data within environments such as operatories or labs.

The inventor hereby incorporates the above-referenced patents and patent applications into his specification.

SUMMARY OF THE INVENTION

The present invention is a combination dental practice management and charting system and dental imaging system which includes a dental imaging device that is in bi-directional communication with a dental practice management and charting system.

In a first aspect of the present invention the combination dental practice management and charting system and dental imaging system overcomes much of the complexities of interaction between the dental imaging system and the dental practice management and charting system and automates related tasks between these two disparate In a second aspect of the present invention the dental imaging system has bi-directional communication capabilities with the dental practice management and charting system. These communication capabilities include an ADA CDT code that is used to correlate to a type, number and/or format of images to be acquired and/or acquired by the dental imaging device.

In a third aspect of the present invention these communication capabilities include either sending or receiving an ADA CDT code that is used to correlate images acquired from the dental imaging system to either a dental e-claim form or a practice management system electronic charting module.

In a fourth aspect of the present invention a bi-directional communication interface facilitates communication between the dental practice management and the dental imaging system.

In a fifth aspect of the present invention the combination dental imaging system and dental practice management and charting system includes a dental imaging device, a dental practice management and charting system, a bi-directional communication interface, a code generator, a translator and a correlator.

In a sixth aspect of the present invention the code generator is coupled to the dental imaging system and generates an ADA CDT code.

In a seventh aspect of the present invention the translator translates the generated ADA CDT code into at least one property required by the dental imaging system in order to acquire dental images of a specific image type, format and quantity.

In an eighth aspect of the present invention the correlator correlates the images acquired by the dental imaging system to the ADA CDT code so that the images are acquired by having at least one property set.

In a ninth aspect of the present invention the dental imaging system is a 2D dental imaging system.

In a tenth aspect of the present invention the dental imaging system is a 3D dental imaging system.

In an eleventh aspect of the present invention the combination dental practice management and charting system and dental imaging system is fully automatic.

In a twelfth aspect of the present invention the combination dental practice management and charting system and dental imaging system is semi-automatic.

Other aspects and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
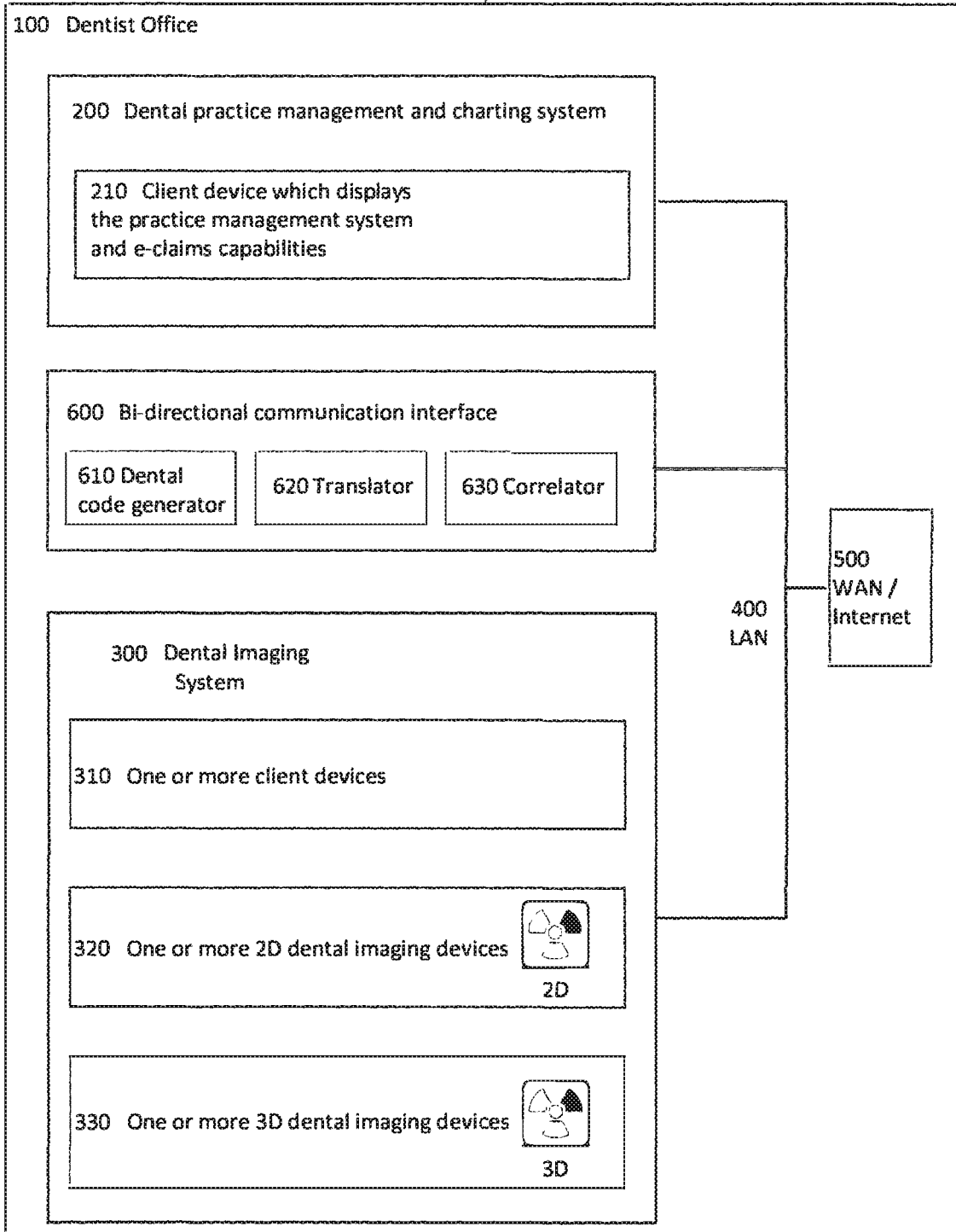
FIG. 1 is a diagrammatic drawing that includes dentist office, a practice management and charting system, a dental imaging system, a LAN connection, a WAN connection, a bi-directional communication interface, a code generator, a translator and a correlator according to the present invention.

Referring to FIG. 1 a dentist office 100 includes a practice management and charting system 200, a dental imaging system 300, a LAN connection 400, a WAN connection 500 and a bi-directional communication interface 600. The practice management and charting system 200 includes at least client device 210 which displays practice management and e-claims capabilities. The dental imaging system 300 includes at least one 3D dental imaging device 330 and/or at least one 2D dental imaging device 320 and at least one client device such as either a client device 310 or a client device 210. Either of these client devices 210 or 310 can display images from the dental imaging system 300. Using the capabilities of the bi-directional communication interface 600 the practice management and charting system 200 is able to bi-directionally communicate with the dental imaging system 300 via LAN 400 or WAN 500.

Still referring to FIG. 1 the bi-directional communication interface 600 includes a code generator 610, a translator 620 and a correlator 630. The bi-directional communication 600 couples the dental imaging system 300 to the dental practice management and charting system 200. The code generator 610 is coupled to the dental imaging system 300 and generates an ADA CDT code. The translator 620 translates the ADA CDT code into at least one property required by the dental imaging system 300 in order to acquire dental images of a specific image type, format and quantity. The correlator 630 correlates the images acquired by the dental imaging system 300 to the ADA CDT code. The images are acquired by having at least one property set.

Figure 2:
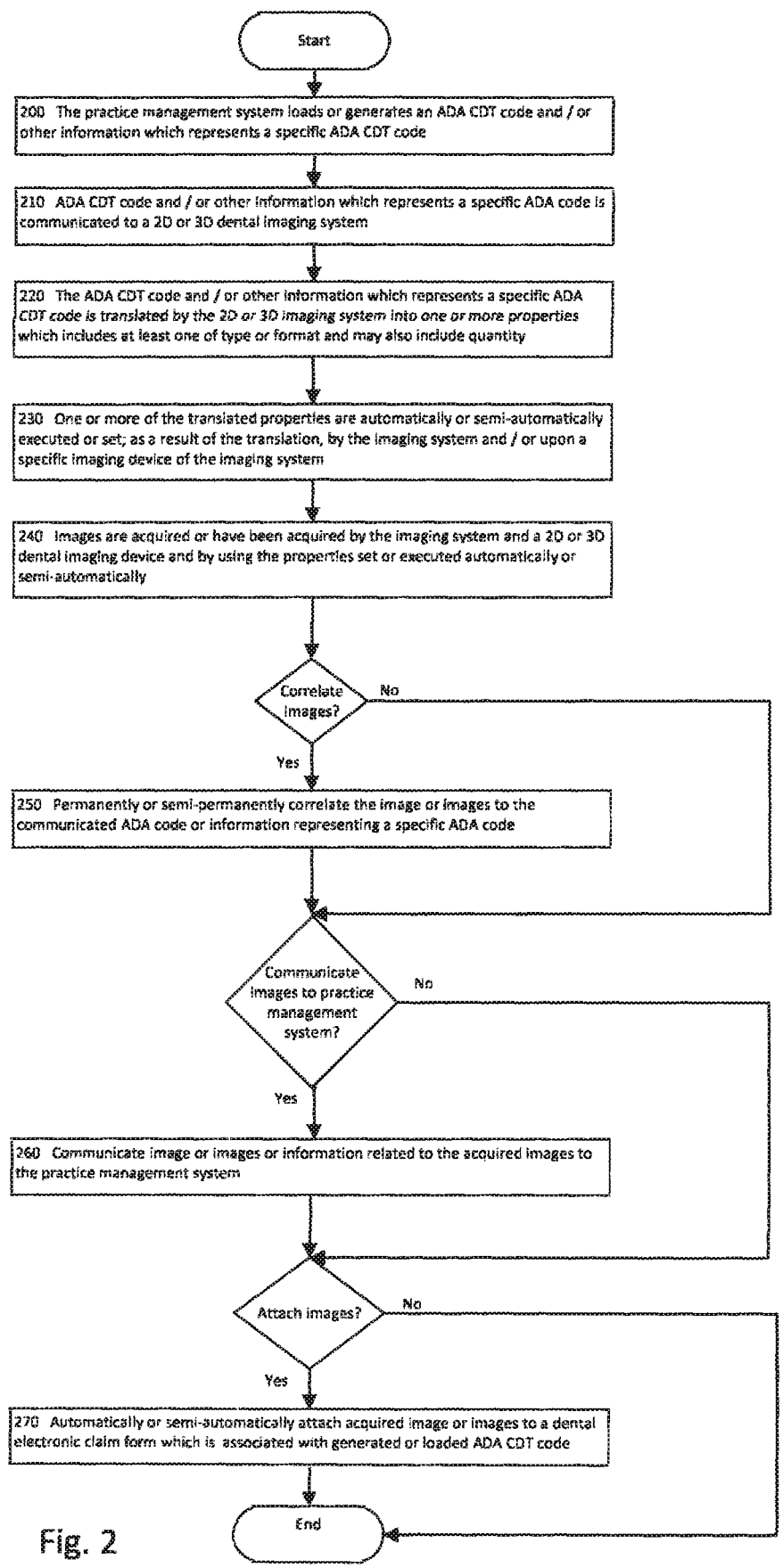
FIG. 2 is a flowchart of the first preferred embodiment of the present invention.

Referring to FIG. 2 in combination with FIG. 1 in step 200 the dental practice management and charting system 200 loads or generates an ADA CDT code and/or other information which represents a specific ADA code. In Step 210 the ADA CDT code is communicated to the dental imaging system. In step 220 the communicated ADA CDT code is translated by the imaging system 300 into at least one property which includes at least one of type, format and may also include quantity. In step 230 at least one translated property is executed or set as a result of the translation by the imaging system 300 and/or upon a specific imaging system 300. In step 240 images are acquired or have been acquired by the imaging system and the dental imaging system 300 by using the properties either set or executed. In step 250 the acquired images may be permanently or semi-permanently correlated to the communicated ADA CDT code. In step 260 the correlated images or information related to the images may optionally be communicated to the dental practice management and charting system 200. In step 270 the images which are correlated to the communicated ADA CDT code and are optionally attached to a dental electronic claim form.

Figure 3:
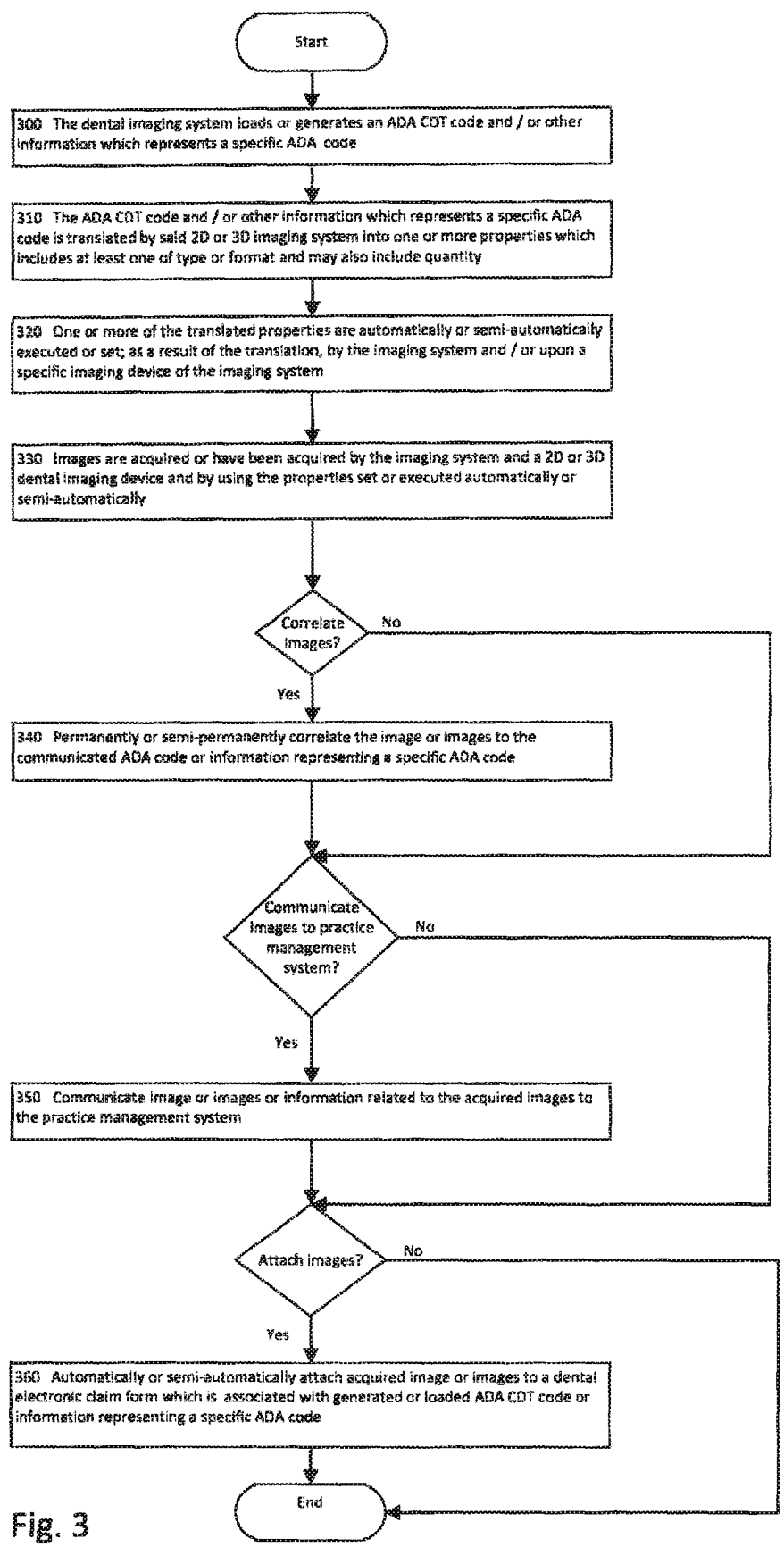
FIG. 3 is a flowchart of the second preferred embodiment of the present invention.

Referring to FIG. 3 in combination with FIG. 1 in step 300 the dental imaging system 300 either loads or generates an ADA CDT code and/or other information which represents a specific ADA CDT code. In Step 310 the ADA CDT code is translated by the imaging system 300 into at least one property which include at least one of type and format, and may also include quantity. In step 320 at least one translated property is either executed or set as a result of the translation by the imaging system and/or upon a specific imaging device 300. In step 330 images are acquired or have been acquired by the dental imaging system 300 using the properties either set or executed. In step 340 the acquired images may be permanently or semi-permanently correlated to the communicated ADA CDT code. In step 350 the correlated images or information related to the images may optionally be communicated to the dental practice management and charting system 200. In step 360 images are correlated to the communicated ADA CDT code and are optionally attached to a dental electronic claim form.

Referring again to FIG. 1 the dental imaging system 300 is selected from a first Markush group which consists of a 2D intraoral x-ray sensor, a 2D extraoral x-ray sensor, a 2D imaging plate scanner, a 2D intraoral video camera, a 2D dental extraoral video camera, a 2D dental intraoral still camera, a 2D dental extraoral still camera, a 3D cone beam, a 3D scanner, a 2D panoramic extraoral x-ray sensor and a 2D cephalometric extraoral x-ray sensor.

The translator 620 generates at least one type from a second Markush group selected which consists of the following translation types: 2 bitewings, 3 bitewings, 4 bitewings, vertical bitewings, intraoral full mouth 18, intraoral full mouth 21, periapical, occlusal, checkup X-ray, intraoral X-ray, extraoral X-ray, TMJ X-ray, facial bone X-ray, panoramic X-ray, oral photograph, facial photograph, cone Beam CT craniofacial, cone beam 2D reconstruction, cone beam 3D reconstruction, CT capture, CT jaw, CT mandible, CT maxilla, CT both, maxillofacial MRI, maxillofacial ultrasound, other, visible light, diagnostic supplement and X-ray additional and photograph additional.

The translation creates a format which is selected from a third Markush group which includes a format that represents color or grayscale image or image data, a format that represents a visual arrangement for display of multiple images and a quantity that represents the physical number of images to acquire. The generated ADA CDT code is either encoded or non-encoded. Each of the properties is translated prior to communication to the dental imaging system by the dental practice management system. The generated code may be represented by a value other than an ADA CDT code. The combination dental imaging system and dental practice management and charting system is either fully automatic or semi-automatic.

By utilizing the methods of the present invention which includes communicating and translating an ADA CDT code between two disparate systems combined with selecting type, format and optionally quantity of images to be acquired and/or correlating acquired images with an e-claim form in the dental practice management and charting system 200, a dentist can greatly improve the efficiency of his dental practice in regards to operation and workflow of the dental practice management and charting system 200 when used in combination with a dental imaging system 300 for the purposed of correlating images to ADA CDT codes and/or e-claims.

From the foregoing it can be seen that a bi-directional communication Interface which couples a dental practice management and charting to a dental imaging system has been described. It should be noted that the sketches are not drawn to scale and that distances of and between the figures are not to be considered significant.

Accordingly, it is intended that the foregoing disclosure and showing made in the drawing shall be considered only as an illustration of the principle of the present invention.

What is claimed is:

1. An improved method for acquiring dental images for a patient, said method comprising the steps of:
  a. using at least one dental imaging device on a patient wherein said dental imaging device produces dental image data;
  b. using a dental imaging system which allows acquisition of images or image data and which is coupled to said dental imaging device;
  c. using a dental charting system capable of generating CDT codes or information that represents such codes;
  d. temporarily coupling two of said systems using a bi-directional interface wherein said bi-directional interface allows communication between said systems;
  e. using said bi-directional communication interface for coupling said dental imaging system to said dental charting system thereby providing communication between said systems thereby facilitating ability to implement automatic initializing of said image acquisition process for the coupled imaging device;

f. using said bi-directional communication interface to communicate a CDT code or data that represents such code to or from said dental charting system which is temporarily coupled to said dental imaging system;

g. using said bi-directional communication interface to communicate a patients first name, last name and identification number from said decoupled and disparate charting system to the currently coupled dental imaging system wherein said first name, last name and identification number were generated by said disparate charting system and wherein said imaging system software analyzes the communicated patient information and detects whether the patient already exists in the disparate imaging system and, if the patient exists, programmatically selects that patient for correlation with the images to be acquired and, if the patient does not already exists, the patient is added programmatically without user input to said dental imaging system software, and thereby creating a patient reference between said dental imaging system and said dental charting system; and h. using said dental imaging system which acts upon receiving a communicated dental CDT code or data that represents such code from a disparate Charting system and programmatically analyzes and compares the code to a list of CDT codes or data that represents such codes and translates the specific communicated CDT from a diagnostic code into the steps required to initialize the process of acquiring image data from the one or more specific imaging devices currently coupled to the imaging system which are capable of producing the required CDT code diagnostic image or image data.

2. A method for acquiring dental images for a patient according to claim 1 wherein said method also includes the steps of:

a. using a disparate and decoupled dental insurance e-claims submission system which operates upon either said second processor or a third processor and which submits electronic claims forms (e-claims) to an insurance provider and/or insurance clearing house; and b. using a bi-directional communication interface for coupling said dental imaging system to said disparate and decoupled dental insurance submission system thereby providing communication between said systems to facilitate automatic correlation of said dental images or image data generated from said dental imaging system to said disparate and decoupled insurance submission system's electronic e-claim form and wherein the images are found for correlation by communicating at a minimum the patient last name or ID of the disparate imaging system patient references.

3. A method for acquiring dental images for a patient according to claim 2 wherein said method also includes the step of using software which automatically associates said image(s) and image metadata which were acquired via said communication of a CDT code or other data that represents such code between said disparate and decoupled dental charting system and dental imaging system wherein said acquired images are associated with said software of said e-claims submission system automatically without requiring user input.

4. A combination dental imaging system, dental charting system and dental insurance e-claim submission system comprising:

a. a dental charting system including electronic dental charting software;

b. a dental insurance submission system including electronic claim submission capabilities (e-claim) and being coupled to said dental charting system wherein said dental insurance submission system has an image attachment capability for attaching and electronically transmitting images with a patient's specific e-claim;

c. a plurality of dental imaging devices each of which can generate dental images or image data and each of which is coupled to said dental charting system;

d. a dental imaging system including imaging software decoupled from said dental charting system software wherein said dental imaging software can acquire dental images or image data from one or more of said dental imaging devices coupled to said dental imaging system; and e. a bi-directional communication interface allowing communication between said dental charting system and said dental imaging devices of said dental imaging system wherein said combination dental imaging system, dental charting system and dental insurance e-claim submission system also includes:

i. a data communication interface allowing data transfer between said dental charting system and said dental imaging device of said dental imaging system;

ii. a code generator which generates either an ADA CDT code or another code representing such ADA CDT code;

iii. a translator which translates either said ADA CDT code or said other code into parameters required by said dental imaging system and said dental imaging devices to configure each of said dental imaging devices to perform an image acquisition;

iv. imaging software which initiates acquisition from said dental imaging device using parameters from said translated CDT code; and v. a correlator which correlates the automatically acquired dental images or image data to said dental e-claims submission system whereby either automatic or semi-automatic submission (transfer) of said correlated dental images to said e-claims system recipient along with either a CDT code or another code representing such code.

5. An improved method for acquiring dental images for a patient according to claim 1 wherein said dental imaging system is disparate and decoupled from said dental imaging device and is also disparate and decoupled from said dental charting system.

6. A combination dental imaging system, dental charting system and dental insurance e-claim submission system according to claim 4 wherein said dental charting system is disparate and decoupled from said dental insurance e-claim submission system.

* * * * *